ём
United States Patent [19]

Huth et al.

[11] Patent Number: 5,506,234
[45] Date of Patent: Apr. 9, 1996

[54] β-CARBOLINE DERIVATIVES FOR USE AS PHARMACEUTICAL AGENTS

[75] Inventors: Andreas Huth; Dieter Seidelmann; Dieter Rahtz; Ralph Schmiechen; Herbert Schneider; Lechoslaw Turski, all of Berlin, Germany

[73] Assignee: Schering Aktiengesellschaft, Berlin, Germany

[21] Appl. No.: 943,177

[22] Filed: Sep. 14, 1992

[30] Foreign Application Priority Data

Sep. 13, 1991 [DE] Germany ............... 41 30 933.2

[51] Int. Cl.$^6$ ...................................... A61K 31/44
[52] U.S. Cl. ............................................ 514/292
[58] Field of Search ........................ 546/85, 86, 87; 514/292, 98, 228.8, 230.8

[56] References Cited

U.S. PATENT DOCUMENTS

| | | | |
|---|---|---|---|
| 4,435,403 | 3/1984 | Braestrup et al. | 546/85 |
| 4,596,808 | 6/1986 | Braestrup et al. | 514/292 |
| 4,623,649 | 11/1986 | Huth et al. | 514/292 |
| 4,644,062 | 2/1987 | Haffer et al. | 546/85 |
| 4,645,773 | 2/1987 | Engelstoft et al. | 514/292 |
| 4,731,365 | 3/1988 | Biere et al. | 514/222 |
| 4,757,070 | 7/1988 | Biere et al. | 514/228.2 |
| 4,877,792 | 10/1989 | Biere et al. | 514/292 |
| 4,933,345 | 6/1990 | Huth et al. | 514/253 |
| 4,960,777 | 10/1990 | Biere et al. | 514/253 |
| 5,145,847 | 9/1992 | Bohlmann et al. | 514/182 |

OTHER PUBLICATIONS

Neef et al., Heterocycles 20(7), 1983. pp. 1295–1313.

Primary Examiner—Raymond Henley, III
Assistant Examiner—Phyllis G. Spivack
Attorney, Agent, or Firm—Millen, White, Zelano, & Branigan

[57] ABSTRACT

β-carbolines of formula I are described

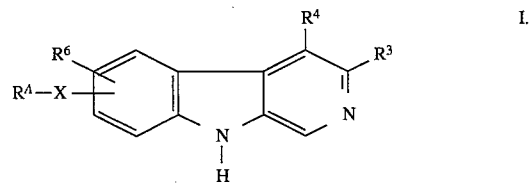

in which
R$^A$ is a C$_{6-12}$ aryl hetaryl as defined herein, that can be substituted singly to multiply with halogen, C$_{1-4}$-alkoxy, C$_{1-4}$-alkyl or amino,
X is —(CH$_2$)$_n$— or —C≡C—,
for use as pharmaceutical agents.

5 Claims, No Drawings

β-CARBOLINE DERIVATIVES FOR USE AS PHARMACEUTICAL AGENTS

BACKGROUND OF THE INVENTION

The invention relates to new β-carbolines aralkylated, arylated or alkinylated in the A ring, their production and use in pharmaceutical agents.

It is known from numerous publications that β-carbolines bind to the benzodiazepine receptors and can be used as psychopharmaceutical agents.

Thus, in EP-54 507 (corresponding to U.S. Pat. Nos. 4,435,403 and 4,596,808), 6-(phenylethinyl)-β-carboline-3-carboxylic acid ethyl ester and in EP-A-137 390 (corresponding to U.S. Pat. No. 4,623,649) others with phenyl, benzyl or phenethyl-substituted β-carbolines are described. However, these compounds do not show the metabolic stability required for a pharmaceutical agent.

The compounds according to the invention are distinguished by good affinity to the benzodiazepine receptors and by their metabolic stability.

SUMMARY OF THE INVENTION

The invention relates to the compounds of formula I

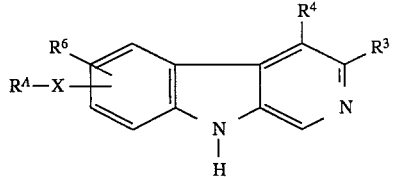

in which $R^A$ is a $C_{6-12}$ aryl or hetaryl, that can be substitued singly to multiply with halogen, $C_{1-4}$-alkoxy, $C_{1-4}$-alkyl or amino X is $—(CH_2)_n—$ or $—C≡C—$ $R^6$ is hydrogen, halogen or $C_{1-4}$-alkoxy, $R^4$ is hydrogen, $C_{1-4}$-alkyl or $—(CH_2)_m—O—(CH_2)_p—R$ and $R^3$ is $—CO_2—C_{1-6}$-alkyl, $—CO—R^2—COOH$ or

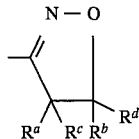

and n is 0, 1 or 2 m is 1 or 2 p is 1, 2, 3 or 4,

R is hydrogen or $C_{1-2}$-alkoxy, $R^2$ is $C_{1-4}$-alkyl, or $C_{3-7}$-cycloalkyl optionally subsituted with methyl or an mono- or bicyclic $C_{6-12}$-aryl radical optionally substituted with $C_{1-4}$-alkyl, $C_{1-4}$-alkoxy or amino, $R^a$ and $R^b$ are the same or different and each mean hydrogen, $C_{1-6}$-alkoxy, $C_{1-6}$-alkyl, $—CH_2—O—C_{1-4}$-alkyl, phenyl or benzyl and $R^c$ and $R^d$ each mean a hydrogen or together a bond, with the proviso that $R^3$ is not $—COOC_2H_5$:

(i) if $R^6$ and $R^4$ are hydrogen and $—X—R^A$ is 6-phenethinyl, 5-phenyl or 5-benzyl;

(ii) if $R^6$ is hydrogen, $R^4$ is methyl and $—X—R^A$ is benzyl, phenyl or 6-phenethyl or (iii) if $R^6$ is hydrogen, $R^4$ is methoxymethyl and $—X—R^A$ is 5-benzyl.

Also included in the above invention are isomers and acid addition salts of the above formula.

Substituents $R^AX$ and $R^6$ can be in 5–8 position in the A ring. The 5 or 6 position is preferred for substituent $R^AX$. For substituent $R^6$, which can be substituted once to twice, the 6- and/or 7 position is preferred.

Alkyl denotes both straight-chain and branched-chain radicals each such as, for example, methyl, ethyl, propyl, isopropyl, butyl, isobutyl, sec. butyl, tert. butyl, pentyl, isopentyl and hexyl.

Halogen is understood to mean in each case flourine, chlorine, bromine and iodine.

Cycloalkyl can stand for cyclopropyl, cyclobutyl, cyclopentyl, cyclohexyl, cycloheptyl and 2-methylcyclopropyl in each case, and preferably is 3–5 carbon atoms.

If $R^A$ means a hetaryl radical, the latter is 5 or 6-membered and contains 1–3 heteroatoms such as nitrogen, oxygen and/or sulfur. For example, the following 5 and 6-ring hetaryl residues can be mentioned: pyridine, pyrimidine, pyrazine, pyridazine, furan, thiophene, pyrrole, thiazole, imidazole, triazine.

Hetaryl radical $R^A$ can be not only monocyclic but also bicyclic, especially a fused benzene ring, such as, for example, benzofuran, benzimidazole, quinoline, quinoxaline, or isoquinoline.

$R^A$ or $R^2$ mean an aryl radical, the latter can be monocyclic or bicyclic, such as, for example, phenyl, biphenyl, naphthyl, indenyl. Monocyclic radicals $R^A$ are considered preferable.

The substituents on aryl or hetaryl radicals may be in any position, are preferably present once or twice and do not have to be identical. Preferred are compounds in which $R^3$ is $—CO_2—C_{1-6}$-alkyl; isoxazole optionally substituted with $C_{1-6}$-alkoxy, $C_{1-6}$-alkyl or $—CH_2—O—C_{1-4}$-alkyl; $—CO—R^2$ in which $R^2$ is $C_{3-5}$-cycloalkyl optionally substituted with methyl, or is phenyl optionally substituted with $C_{1-4}$-alkyl, $C_{1-4}$-alkoxy or amino.

The physiologically compatible acid addition salts are derived from known inorganic and organic acids such as, for example, hydrochloric acid, hydrobromic acid, sulfuric acid, phosphoric acid, formic acid, acetic acid, benzoic acid, maleic acid, fumaric acid, succinic acid, tartaric acid, citric acid, oxalic acid, glyoxylic acid as well as alkane sulfonic acids and aryl sulfonic acids such as, for example, methane sulfonic acid, ethane sulfonic acid, benzene sulfonic acid, p-toluene sulfonic acid, i.a.

The compounds of formula I as well as their acid addition salts are useful as a pharmaceutical agents because of their affinity for benzodiazepine receptors. The compounds of formula I are distinguished by selective anxiolytic effectiveness with a very slight probability for side effects, since they do not have other effects typical for benzodiazepines such as anticonvulsive effectiveness.

The affinity to the benzodiazepine receptors is determined by examining the displacement capacity of radioactively labeled benzodiazepine from the benzodiazepine receptors. To examine the anxiolytic effect the compounds are tested in the 4-plate test according to the method of Boissier et al. Eur. J. Pharmacol. 4, 145–150 (1968). Thus the minimal effective dose (MED) is indicated that increases the locomotive activity of the afflicted mice after i.p. treatment.

TABLE

| compound | MED mg/kg i.p. |
|---|---|
| A | 0.78 |
| B | 1.56 |

A = 5-(3-pyridyl)-4-methoxymethyl-β-carboline-3-carboxylic acid isopropyl ester
B = 6-phenyl-4-methoxymethyl-β-carboline-3-carboxylic acid isopropyl ester The compounds of formula I are suitable as psychopharmaceutical agents in human medicine, and are used especially for the treatment of anxiety conditions accompanied by depression. Memory-promoting properties are also found in the compounds according to the invention.

To use the compounds according to the invention as pharmaceutical agents, the compounds are put in the form of a pharmaceutical preparation, that contains, in addition to the active ingredient for the enteral and parenteral administration, suitable pharmaceutical, organic or inorganic inert vehicles such as, for example, water, gelatin, gum arabic, lactose, starch, magnesium stearate, talc, vegetable oils, polyalkylene glycols, etc. The pharmaceutical preparations can be available in solid form, for example, as tablets, coated tablets, suppositories, capsules, or in liquid form, for example, as solutions, suspensions or emulsions. Optionally, moreover, they contain auxiliary agents such as preservatives, stabilizers, wetting agents or emulsifiers, salts for changing the osmotic pressure or buffers.

Injection solutions or suspensions, especially aqueous solutions of the active compounds in polyhydroxy-ethoxylated castor oil, are especially suitable for parental application.

Auxiliary agents such as salts of bile acids or animal or vegetable phospholipids, and mixtures thereof as well as liposomes or their components can be used as vehicle systems.

For oral use, tablets, coated tablets, or capsules with talcum and/or hydrocarbon vehicles or binders, such as, for example, lactose, corn or potato starch, are especially suitable. The vehicle can be in liquid form, such as, for example, as juice to which a sweetner is optionally added.

The compounds according to the invention are introduced in a dosage unit of 0.05 to 100 mg of active substance in a physiologically compatible vehicle.

The compounds according to the invention in general are used in a dose of 0.1 to 300 mg/day, preferably 0.1 to 30 mg/day, especially preferred 1–20 mg/day, and 0.001–6/kg body weight/day, preferably 0.001–0.6 mg/kg/day, more preferably 0.001–0.3 mg/kg/day, for example as anxiolytic agents, analogously to diazepam.

The production of the compounds according to the invention takes place according to methods known in the art, for example compounds of formula I are produced by a process wherein a) a compound of formula II

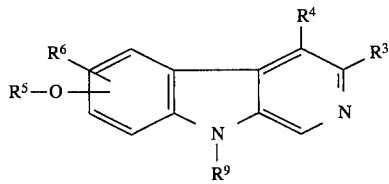

in which
R$^3$, R$^4$ and R$^6$ have the above meaning
R$^9$ is a hydrogen or a protective group and
R$^5$ is a leaving group,
is reacted in the presence of a nickel or palladium catalyst with an organometallic compound of formula III $$R^A\text{—Me—}X_r \qquad \text{III.}$$

in which R$^A$ has the above meaning,
Me represents a metal atom,
X represents hydroxy, C$_{1-4}$ alkyl, halogen or R$^A$ and
r represents a number from 1 to 3, or b) a compound of formula IV

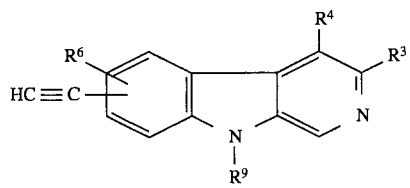

in which
R$^3$, R$^4$, R$^6$, and R$^9$ have the above meaning is reacted in the presence of a nickel or palladium catalyst with halogenated R$^A$ c) a compound of formula V

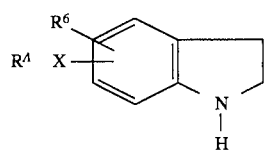

in which
R$^A$, X and R$^6$ have the above meaning, is reacted with a azadiene of formula VI

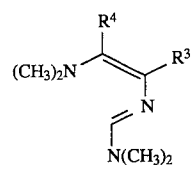

in which R$^3$ and R$^4$ have the above meaning, or d) a compound of formula VII,

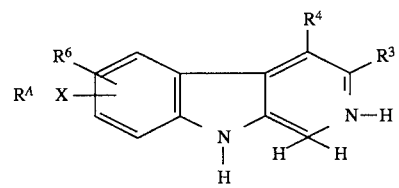

in which R$^A$, X, R$^3$, R$^4$ and R$^6$ have the above meaning is dehydrogenated or e) a compound of formula VIII

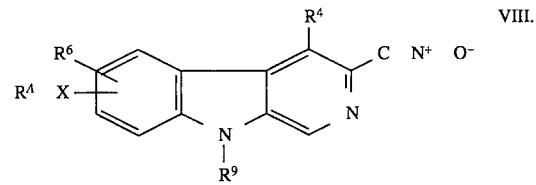

in which R$^A$X, R$^4$, R$^6$ and R$^9$ have the above meaning is cyclized or optionally halogenated with a compound of formula IX

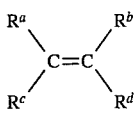

IX.

in which $R^a$, $R^b$, $R^c$ and $R^d$ have the above meaning, or f) a compound of formula X

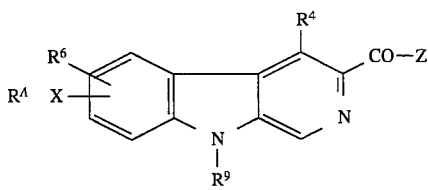

X.

in which $R^A$, X, $R^4$, $R^6$ and $R^9$ have the above meaning and Z is hydrogen, $C_{1-4}$-alkoxy or a reactive acid derivative, is reacted with an organometallic compound to compounds of formula I with $R^3$=CO—$R^2$ and optionally oxidized as well as then optionally protective group $R^9$ is cleaved off or a —C≡C— bond is reduced or $R^3$=$CO_2C_{1-6}$-alkyl is transesterified or saponified or the isomers are separated or the acid addition salts are formed.

For the process variants a) and b) suitable nickel and palladium catalysts are, for example, 1,3-diphenylphosphinopropane-nickel-11-chloride, bis-tri-o-tolylphosphine-palladium-II-chloride, bis-triphenylphosphine-palladium-II-chloride, tetrakistriphenylphosphine-palladium-(O), 1,1'-bis-diphenylphosphinoferrocene-palladium-II-chloride and bis[tri-(2-methylphenyl)-phosphine]-palladium-II-chloride. As the organometallic compounds in process variant a) lithium, boron, magnesium, zinc or tin derivatives can be used and substituent X can be one to three each according to the valance of the metal atom and X as halogen is especially chlorine or bromine. As solvents, inert solvents, for example, cyclic and acyclic ethers, hydrocarbons or aprotic polar solvents are suitable and when using boron also protic solvents such as alcohols.

As the volatile group $R^5$ trifluoromethane sulfonyl is especially suitable. If a protective group $R^9$ (alkyl, benzyl-, alkanoyl, trialkylsilyl, arylsulfonyl, alkylsulfonyl such as tosyl, mesyl, trimethylsilyl, tert. butyl-di-methylsilyl, tert. butoxycarbonyl) is desired, then the latter can be introduced in each case by the usual alkylation, acylation, silylation or sulfonylation processes such as, for example, by reaction with the corresponding anhydrides or halides.

The reaction according to process variant a) takes place at temperatures of 0° C. to the boiling temperature of the reaction mixture in the presence of bases such as organic amines or alkali carbonates or alkali hydroxides. Optionally an addition of lithium chloride and/or Cu-I-iodide is advantageous.

The substitution of the ethinyl derivatives according to process variant b) take place in the presence of bases such as secondary or tertiary amines or alkali carbonates or alkali hydroxides in the presence of a nickel or palladium catalyst as stated above at temperatures up to the boiling temperature of the reaction mixture. As halogen derivative bromine and iodine compounds are especially used. Thus the used amine can be used as solvent or aprotic solvents are added such as, for example, dimethylformamide, dioxane, acetonitrile, tetrahydrofuran, N-methylpyrrolidone. An addition of Cu-I-iodide or tri-o-tolylphosphine in some reactions has proven itself beneficial.

In process variant c) indoles are reacted with azabutadienes according to H. Biere et al. Liebigs Ann. Chem. 1986 1749–1764, in which the reaction is performed in the presence of acids, optionally in an inert solvent, at higher temperature up to the boiling temperature of the reaction mixture.

If the compounds according to the invention are produced according to process variant d), this takes place according to the process described in EP-190 987 (corresponding to U.S. Pat. No. 4,644,062) by dehydrogenating with tert. butylhypochlorite in an inert solvent at temperatures of –70° C. up to room temperature.

The cycloaddition described in process variant e) takes place according to processes described in EP-A- 305322 (corresponding to U.S. Pat. No. 4,933,345), by converting the corresponding oximes with N-bromosuccinimide, butoxychlorite or Na-hypohalide into the hydroxamic acid halides and hydrogen halide being cleaved off from them with bases. In this way halogenation can also occur in the A-ring of the carboline. To the nitril oxides thus obtained the compound of formula IX is added at temperatures of 0°–40° C. in an aprotic solvent and a protective group can be present in the 9-position of the carboline.

The compounds of formula I with $R^3$ meaning —CO—$R^2$ can be produced according to the process described in PCT/DE 90/00982 by an organometallic compound such as a Grignard-compound $R^2Mg$ halogen or a lithium-organic compound $R^2Li$ being reacted at temperatures of –70° C. up to room temperature in aprotic polar solvents or hydrocarbons. Amides such as imidazolides but also esters are suitable as reactive acid derivatives. If the aldehyde protected in 9 position is used, the resulting alcohol can be oxidized to ketone in a known way according to PCT/DE 90/00982.

If a protective group $R^9$ is present, the latter can be cleaved off depending on the type of protective group by the usual methods such as by treatment with acids such as diluted mineral acids or organic acids or with bases such as alkali hydroxides or alkali alcoholates or with fluorides such as cesium fluoride or tetrabutyl ammonium fluoride optionally during the working-up of the reaction mixture.

The reduction of the triple bond takes place catalytically with Raney-Nickel or palladium/carbon at room temperatures under normal pressure or higher pressure in alcohols such as aliphatic alcohols.

If a transesterification is desired, the methods described in EP-A-237 467 (corresponding to U.S. Pat. Nos. 4,877,792 and 4,960,777) can be used by transesterification with alkali alcoholates or the corresponding alcohol, optionally by addition of titanium-tetra-isopropylate as catalyst at higher temperature. The introduction of the tert. butylester group takes place, e.g., by reaction of the carboxylic acid with tert. butoxy-bis-dimethyl-amminomethane. The hydrolysis of the ester group can take place in an acid or alkaline manner in the usual way, for example, with Na- or K-hydroxide in protic solvents or according to the process described in EP-A-161 574 (corresponding to U.S. Pat. No. 4,645,773).

The mixture of the isomers can be separated according to usual methods such as, for example, crystallization, chromatography or salt formation.

For the formation of physiologically compatible acid addition salts a compound of formula I is dissolved for example in a little alcohol and mixed with a concentrated solution of the desired acid.

If the production of the intial compounds is not described, these compounds are known or can be produced by known or analogously to known compounds or by the processes described here.

For example the production of the ethinyl derivates of formula II is described in EP-A-54507.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

The entire disclosure of all applications, patents and publications, cited above, and of corresponding German application P 41 30 933.2, are hereby incorporated by reference.

EXAMPLES

Initial compounds

A) 5-Trifluoromethanesulfonyloxy-4-methoxymethyl-9-trifluoromethanesulfonyl-carboline- 3-carboxylic acid ethyl ester 5.4 g of 5-hydroxy-4-methoxymethyl-β-carboline-3-carboxylic acid ethyl ester and 7.5 g of N,N-dimethylaminopyridine are dissolved in 250 ml of methylene chloride and cooled to 0° C. A solution of 6.5 ml of trifluoromethanesulfonic acid anhydride in 40 ml of methylene chloride is slowly instilled in this mixture at 0° C. solution temperature. After stirring for ½ hour at 0° C. it is mixed in succession with 100 ml of water and 50 ml of 1-N hydrochloric acid and shaken out. The organic phase in succession is washed with 1-N hydrochloric acid and water, dried and concentrated by evaporation. The residue is recrystallized from hexane and a little ethyl acetate and yields 8.2 g (80% of theory) of 5-trifluoromethanesulfonyloxy- 4-methoxymethyl-9-trifluoromethanesulfonyl-β -carboline-3-carboxylic acid ethyl ester of a melting point of 60°–62° C.

In an analogous way there are produced:

6-trifluoromethanesulfonyloxy-4-methoxymethyl-9-trifluoromethanesulfonyl-β -carboline-3-carboxylic acid isopropyl ester, melting point 80°–82° C.

5-trifluoromethanesulfonyloxy-4-methoxymethyl-9-trifluoromethanesulfonyl-β -carboline-3-carboxylic acid isopropyl ester.

B) 6-Trifluoromethanesulfonyloxy-4-methoxymethyl-9-tert.-butoxycarbonyl-β -carboline-3-carboxylic acid isopropyl ester 2.5 g of 6-benzyloxy-4-methoxymethyl-β-carboline-3-carboxylic acid isopropyl ester is dissolved in 100 ml of methylene chloride and mixed in succession with 0.76 g of N,N-dimethylaminopyridine and a solution of 3.2 g of di-tert.butyldicarbonate in 25 ml of methylene chloride at 0° C. After stirring 2 hours in succession it is washed with saturated sodium carbonate solution and saturated common salt solution, dried, filtered and concentrated by evaporation. The residue is chromatographed on silica gel with methylene chloride:ethanol=10:1 and yields 4.7 g (75% of theory) of 6-benzyloxy-4-methoxymethyl-9-tert.butoxy-carbonyl-β -carboline-3-carboxy acid isopropyl ester, which is hydrogenated in 50 ml of methanol/tetrahydrofuran=1:1 with 0.5 g of palladium/carbon (10%) under hydrogen standard pressure at room temperature. The batch is filtered over diatomaceous earth, concentrated by evaporation and the residue absorptively precipitated. 3.6 g (91% of theory) of 6-hydroxy-methoxymethyl-9tert.-butoxycarbonyl-β-carboline-3-carboxylic acid isopropyl of a melting point of 183°–186° C. is obtained. 2 g of this substance together with 1.1 g of N,N-dimethylaminopyridine is dissolved in 100 ml of methylene chloride and slowly mixed with a solution of 0.85 ml of trifluoromethanesulfonic acid anhydride in 10 ml of methylene chloride. After stirring for 1 hour at 0° C. it is in succession washed with saturated sodium bicarbonate solution and saturated common salt solution, dried, filtered and concentrated by evaporation. The residue is chromatographed on silica gel with methylene chloride:ethanol=10:1 and after recrystallization from hexane yields 2.3 g (88% of theory) of 6-trifluoromethanesulfonyloxy-4-methoxymethyl- 9-tert.-butoxy-carbonyl-β-carboline-3-carboxylic acid isopropyl ester of a melting point of 105° C.

In an analogous way there is produced:

5-trifluoromethanesulfonyloxy-4-methoxy-9-tert.butoxycarbonyl-β -carboline-3-carboxylic acid isopropyl ester.

C) 6-Ethinyl-4-methoxymethyl-β-carboline-3-carboxylic acid isopropyl ester 2.1 g of 6-iodo-4-methoxymethyl-β-carboline-3-carboxylic acid isopropyl ester is mixed in 30 ml of dimethylformamide in succession with 1.53 ml of trimethylsilylacetylene, 15 ml of triethylamine, 50 mg of copper (I) iodide and 100 mg of tetrakis (triphenylphosphine)-palladium (O) and heated for 3 hours under argon to 60° C. solution temperature. After removal of the solvent the residue is taken up in ethyl acetate and in succession is washed with saturated sodium bicarbonate and common salt solution. The organic phase was dried, filtered and concentrated by evaporation and the residue is chromatographed on silica gel with methylene chloride:ethanol=12:1. The correspondingly combined fractions are stirred for 1 hour in 50 ml of methylene chloride with 4 ml of tetrabutylammonium fluoride at room temperature. The solution is washed with water, dried, filtered and concentrated by evaporation and the residue is chromatographed on silica gel with methylene chloride:ethanol= 10:1. 830 mg of 6-ethinyl-4-methoxymethyl-β -carboline-3-carboxylic acid isopropyl ester, melting point 191°–193° C. (ethyl acetate/hexane) is obtained by the corresponding combination of the fractions.

D) 6-Iodo-4-methoxymethyl-β-carboline-3-carboxylic acid isopropyl ester

It is produced according to the process described in Tetr.43(6), 1017, (1987) from 4-methoxymethyl-β-carboline- 3-carboxylic acid isopropyl ester. Melting point 233°–235° C. (ethanol/water).

EXAMPLE 1

5-(2-Thienyl)-4-methoxymethyl-β-carboline-3-carboxylic acid isopropyl ester 423 mg of 5-trifluoromethanesulfonyloxy-4-methoxymethyl- 9-trifluoromethanesulfonyl-β-carboline-3-carboxylic acid ethyl ester is mixed in 15 ml of toluene with 27 mg of tetrakis(triphenylphosphine)-palladium(O) and 0.75 ml of a 2-m sodium carbonate solution. Then a solution of 96 mg of thiophene-2-boronic acid in 3 ml of ethanol is added to the batch and refluxed for 1 hour. After standing overnight it is mixed with 30 ml of water and shaken out three times with ethyl acetate. The combined organic phase is dried, filtered and concentrated by evaporation. The residue is stirred in 15 ml of dichloromethane with 2.25 ml of tetrabutylammoniumfluoride for 2 hours at room temperature. Then it is made alkaline with aqueous ammonia and extracted twice with methylene chloride. The organic phase is washed with water, dried, filtered and concentrated by evaporation. The residue is refluxed for 1.5 hours in 10 ml of i-propanol with 114 mg of titanium (IV)-isoproxide. After concentration by evaporation it is taken up in 25 ml of 1-N hydrochloric acid and extracted three times from ethyl acetate. The organic phase is washed with dilute ammonia solution, dried, filtered and concentrated by evaporation. The residue is chromatographed on silica gel with acetone:hexane=1:1 as eluant. After combining the corresponding fractions and recrystallization from ether 116 mg (40.7% of theory) of 5-(2-thienyl)-4-methoxymethyl-β-carboline-3-carboxylic acid isopropyl ester of a melting point of 160°–162° C. is obtained.

In an analogous way there are produced:

5-(4-Methoxyphenyl)-4-methoxymethyl-β-carboline-3-carboxylic acid isopropyl ester of a melting point of 201°–202° C.

5-(3-thienyl)-4-methoxymethyl-β-carboline-3-carboxylic acid isopropyl ester of a melting point of 145°–148° C.

5-(3-aminophenyl)-4-methoxymethyl-β-carboline-3-carboxylic acid isopropyl ester as oil 5-(2-furyl)-4-methoxymethyl-β-carboline-3-carboxylic acid isopropyl ester of a melting point of 185°–188° C.

5-(2,4-dichlorophenyl)-4-methoxymethyl-β-carboline-3-carboxylic acid isopropyl ester of a melting point of 191°–192° C.

5-(4-chlorophenyl)-4-methoxymethyl-β-carboline-3-carboxylic acid isopropyl ester of a melting point of 200°–202° C.

5-(Phenyl)-6,7-dimethoxy-4-methoxymethyl-β-carboline- 3-carboxylic acid isopropyl ester of a melting point of 182°–183° C.

5-(3-Pyridyl)-4-methoxymethyl-β-carboline-3-carboxylic acid isopropyl ester of a melting point of 187°–188° C.

EXAMPLE 2

5-(3-Pyridyl)-4-methoxymethyl-β-carboline-3-carboxylic acid isopropyl ester 532 mg of 5-trifluoromethanesulfonyloxy-4-methoxymethyl- 9- tert.butoxycarbonyl-β-carboline-3-carboxylic acid isopropyl ester is mixed in 20 ml of toluene in succession with 164 mg of diethyl-3-pyridylborane, 36 mg of tetrakis (triphenylphosphine) palladium (O), 84 mg of lithium chloride, 4 ml of ethanol as well as 2 ml of a 2-m aqueous sodium carbonate solution and refluxed for 3.5 hours. Then borane, palladium catalyst, ethanol, lithium chloride as well as soda solution are added again and heated for 3.5 hours to 120° C. solution temperature. Then it is mixed with 30 ml of water and extracted three times with 30 ml of ethyl acetate. The organic phase is dried, filtered and concentrated by evaporation. The residue is stirred with 13 ml of trifluoroacetate acid for 1 hour at room temperature. After concentration by evaporation it is taken up in 50 ml of dilute sodium carbonate solution and extracted three times with 30 ml of ethyl acetate. The organic phase is washed with water, dried, filtered and concentrated by evaporation. The residue is chromatographed successively twice on silica gel, first with eluant methylene chloride:ethanol=10:1 and then the corresponding fractions on a second column with toluene: glacial acetic acid: water=10:1:1. The corresponding combined fractions are concentrated by evaporation and the residue is refluxed for 1.5 hours with 10 ml of isopropanol and 45 mg of titanium (IV) isopropylate. After concentration by evaporation it is taken up in 15 ml of 1-N hydrochloric acid and extracted three times with 30 ml of ethyl acetate each. The combined organic phase is discarded. The aqueous phase is made alkaline with ammonia and extracted three times with ethyl acetate. The organic phase is dried, filtered and concentrated by evaporation and 45 mg (12% of theory) of 5-(3-pyridyl)-4-methoxymethyl-β-carboline-3-carboxylic acid isopropyl ester with a melting point of 187°–188° C. is obtained.

In an analogous way, but without the transesterification unnecessary in these cases, there are produced:

6-(3-Pyridyl)-4-methoxymethyl-β-carboline-3-carboxylic acid isopropyl ester of the melting point of 230°–232° C.;

6-(2-furyl)-4-methoxymethyl-β-carboline-3-carboxylic acid isopropyl ester of the melting point of 240° C. (decomposition);

6-(4-methoxyphenyl)-4-methoxymethyl-β-carboline-3-carboxylic acid isopropyl ester of the melting point of 235° C.;

6-(2,4-dichlorophenyl)-4-methoxymethyl-β-carboline-3-carboxylic acid isopropyl ester of the melting point of 220°–221° C.;

6-(phenyl)-4-methoxymethyl-β-carboline-3-carboxylic acid isopropyl ester of the melting point of 188°–189° C.;

6-(4-chlorophenyl)-4-methoxymethyl-β-carboline-3-carboxylic acid isopropyl ester of the melting point of 233°–234° C.

EXAMPLE 3

4-Chlorophenylethinyl-4-methoxymethyl-β-carboline-3-carboxylic acid isopropyl ester 250 mg of 6-ethinyl-4-methoxymethyl-β-carboline-3-carboxylic acid isopropyl ester is mixed in 8 ml of dimethylformamide with 2 ml of triethylamine, 118 mg of anhydrous potassium carbonate, 22 mg of tetrakis (triphenylphosphine)-palladium(O), 7 mg of copper(I)iodide and 149 mg of 4-bromochlorobenzone and then the mixture is heated for 4 hours to 110° C. Then bromochlorobenzene, copper(I)iodide and palladium catalyst are added again and heated for 3 hours to 120° C. solution temperature. After concentration by evaporation it is taken up in ethyl acetate, washed in succession with saturated sodium carbonate and common salt solution each, dried, filtered and concentrated by evaporation. The residue is chromatographed twice in succession on silica gel, first with the mobile solvent toluene:ethanol:water= 80:20:1 and then with the mobile solvent methylene chloride:ethanol=12:1, and the corresponding fractions are combined and used in the next chromatography. 120 mg of 6-(4-chlorophenylethinyl)-4-methoxymethyl-β -carboline-3-carboxylic acid isopropyl ester, melting point of 220°–221° C., is obtained.

In an analogous way there are produced:

6-(Phenylethinyl)-4-methoxymethyl-β-carboline-3-carboxylic acid isopropyl ester, melting point 191°192° C.;

6-(2-pyridylethinyl)-4-methoxymethyl-β-carboline-3-carboxylic acid isopropyl ester, melting point 186°–188° C.;

6-(3-pyridylethinyl)-4-methoxymethyl-β-carboline-3-carboxylic acid isopropyl ester, melting point 201°–202° C.;

6-(4-pyridylethinyl)-4-methoxymethyl-β-carboline-3-carboxylic acid isopropyl ester, melting point 215°–217° C.

EXAMPLE 4

6-(4-Chlorophenylethyl)-4-methoxymethyl-β-carboline-3-carboxylic acid isopropyl ester 100 mg of 6-(4-chlorophenylethinyl)-4-methoxymethyl-β-carboline-3-carboxylic acid isopropyl ester is hydrogenated for 1 hour in 20 ml of ethanol with 1 spatula-tip full of Raney nickel (decanted twice with ethanol) at room temperature and hydrogen standard pressure. After filtering off from the catalyst on silica gel it is concentrated by evaporation and the residue is recrystallized from ethyl acetate/hexane. It yields 59 mg (59% of theory) of 6-(4-chlorophenylethyl)-4-methoxymethyl-β-carboline-3-carboxylic acid isopropyl ester, melting point 182°–184° C.

In an analogous way there are produced:

6-Phenylethyl-4-methoxymethyl-β-carboline-3-carboxylic acid isopropyl ester, melting point 149°–151° C.;

6-(2-pyridylethyl)-4-methoxymethyl-β-carboline-3-carboxylic acid isopropyl ester, melting point 150°–151° C.;

6-(3-pyridylethyl)-4-methoxymethyl-β-carboline-3-carboxylic acid isopropyl ester, melting point 142°–143° C.;

6-(4-pyridylethyl)-4-methoxymethyl-β-carboline-3-carboxylic acid isopropyl ester, melting point 149°–151° C.

EXAMPLE 5

6-Phenylethyl-4-methoxymethyl-3-(5-methoxymethylisoxazol-3-yl)-β-carboline 1.2 g of 6-phenethyl-4-methoxymethyl-β-carboline-3-carboxylic acid isopropyl ester is mixed in 25 ml of dry toluene with 2.5 ml of triethylamine and 0.78 ml of chlorotrimethylsilane and heated for 1 hour to 50° C. solution temperature. After concentration by evaporation to about half it is cooled to −78° C. and 5 ml of a 1.2 molar diisobutylaluminium hydride solution is instilled. It is stirred for 30 minutes at −78° C., mixed with 1.2 ml of ethanol and allowed to come to room temperature. 10.2 ml of 0.5-N NaOH and 10.2 ml of ethanol are added to the batch and stirred for 2.5 hours at room temperature. The batch is added to 35 ml of glacial acetic acid and extracted three times from ethyl acetate. The organic phase is washed in succession with dilute ammonia and saturated common salt solution, dried, filtered and concentrated by evaporation. The residue is chromatographed on silica gel with methylene chloride:ethanol= 1:1 and 720 mg of 6-phenethyl-4-methoxymethyl-β -carboline-3-carbaldehyde is obtained, that in 8 ml of dimethylformamide is mixed in succession with 322 mg of hydroxylaminehydrochloride, 1.6 ml of ethanol, 322 mg of powdered potassium hydroxide and refluxed for 3 hours. Suctioning off yields 740 mg of 6-phenylethyl- 4-methoxymethyl-β-carboline-3-carbaldehyde aldoxime of a melting point of 197°–198° C. This oxime is dissolved in 26 ml of dimethylformamide and mixed with a solution of 381 mg of N-bromosuccinimide in 3.4 ml of dimethylformamide and stirred for 15 minutes at room temperature. 1.38 ml of triethylamine and 0.26 ml of methylpropargyl ether is added to the batch and stirred for 7 hours at room temperature. After concentration by evaporation it is spread in ethyl acetate/water and the organic phase is dried, filtered and concentrated by evaporation. The residue is chromatographed on silica gel with toluene:ethanol=9:1. After combining and concentrating by evaporation the corresponding fractions and recrystallization 251 mg (30% of theory) of 6-phenethyl- 4-methoxymethyl-3-(5-methoxymethyl-isoxazol-3-yl)-β -carboline, of a melting point of 133°–135° C. (ethyl acetate) is obtained.

EXAMPLE 6

5-(2-Chlorobenzyl)-β-carboline-3-carboxylic acid ethyl ester

The compound is produced from 4-(2-chlorobenzyl)indole and 3-(dimethylamino)-2-[(dimethylamino)methyleneamino] -acrylic acid ethyl ester according to H. Biere et al. Liebigs Ann. Chem. 1986, 1749–1764, melting point 295°–298° C. (ethanol).

a) 2-(2-Chlorobenzyl)-6-nitrotoluene and 2-(4-chlorobenzyl)- 6-nitrotoluene

A mixture of 25 g (0.15 mol) of 2-methyl-3-nitrobenzyl alcohol and 25 ml (0.22 mol) of tintetrachloride in 250 ml of chlorobenzene is refluxed for 3 hours with stirring. After cooling 50 ml of N-methylpiperazine is slowly instilled. The precipitate is suctioned off and washed several times with ethyl acetate. The combined filtrates are dried on sodium sulfate and concentrated by evaporation and the temperature must not rise above 160° C. The residue (39 g) with a mixture of 33 parts of cyclohexane and 1 part of ethyl acetate is subjected twice to a pressure column chromatography. Thus 9.3 g (24%) of 2-(2-chlorobenzyl)- 6-nitrotoluene, melting point 54°–56° C., and 16 g (41%) of 2-(4-chlorobenzyl)-6-nitrotoluene, melting point 62°–63° C. are obtained.

b) 4-(2-Chlorobenzyl)-indole

A mixture of 16 g (0.06 mol) of 2-(2-chlorobenzyl)-6-nitrotoluene and 24.4 g (0.09 mol) of tripiperidinomethane is heated for 5 hours at 120° C. in a water jet vacuum with interconnection of a distillation assembly. Then the mixture is taken up in 200 ml of a mixture of 5 parts of toluene and 3 parts of glacial acetic acid and under stirring is added to a suspension of 144 g of iron powder and 362 g of silica gel in 800 ml the same toluene-glacial acetic acid mixture. The reaction mixture is refluxed for 1 hour under an argon atmosphere. After cooling it is diluted with methylene chloride and filtered off from a precipitate. The filtrate in succession is washed with 10% sodium carbonate solution, 5% sodium bisulfite solution and saturated common salt solution and then dried on sodium sulfate. The solution is concentrated by evaporation, the residue after chromatography on silica gel with a mixture of 4 parts of cyclohexane and one part of ethyl acetate and recrystallization from cyclohexane yields 9 g (58% of theory) of 4-(2-chlorobenzyl)-indole, melting point 76°–77° C.

Analogously 25.5 g (82% of theory) of 4-(4-chlorobenzyl-indole is obtained from 33.6 g of 2-(4-chlorobenzyl)- 6-nitrotoluene. Melting point 84°–85° C. (from cyclohexane) and this is reacted to 5-(4-chlorobenzyl)-β-carboline- 3-carboxylic acid ethyl ester, melting point 309°–312° C. (from ethanol).

EXAMPLE 7

5-(2-Chlorobenzyl)-β-carboline-3-carboxylic acid isopropyl ester 0.2 g (0.55 mmol) of 5-(2-chlorobenzyl)-β-carboline-3-carboxylic acid ethyl ester is refluxed for 4 hours with 0.16 g (0.57 mmol) of titaniumtetraisopropylate in 50 ml of isopropanol. The solution concentrated by evaporation to half, the isopropyl ester crystallizes out during cooling. Yield 164 mg (79% of theory), melting point 258°–260° C.

Analogously 5-(4-chlorobenzyl)-β-carboline-3-carboxylic acid isopropyl ester is obtained from 5-(4-chlorobenzyl)-β-carboline-3-carboxylic acid ethyl ester, melting point 290°–293° C.

EXAMPLE 8

5-(2-Chlorobenzyl)-4-methoxymethyl-β-carboline-3-carboxylic acid ethyl ester a) 3-[4-(2-chlorobenzyl)-indol-3-yl]-4-methoxy-2-nitrobutyric acid-ethyl ester, 5 g (0.021 mol) of 4-(2-chlorobenzyl)-indole and 20 ml of an about 50% solution containing 2-nitro-3-hydroxy-4-methoxybutyric acid ethyl ester are refluxed for 4 hours in a mixture of 13 g of glacial acetic acid and 500 ml of toluene. 1.7 g (19% of theory) of 3-[4-(2-chlorobenzyl)- 3-yl]-4-methoxy-2-nitrobutyric acid ethyl ester is obtained from the evaporation residue by chromatography with dicloromethane on silica gel, melting point 115°116° C. (from ethanol).

b) 2-Amino-3-[4-(2-chlorobenzyl)-indol-3-yl]-4-methoxybutyric acid ethyl ester, 6.1 g (0.014 mol) of 3-[4-(2-chlorobenzyl)-indol-3-yl]-4-methoxy-2-nitrobutyric acid ethyl ester is hydrogenated in 125 ml of ethanol with 6 g of Raney nickel at standard pressure and room temperature. After 4½ hours the hydrogen absorption is completed. The Raney nickel is filtered off, the filtrate is concentrated by evaporation and a crude product of 5.2 g of 2-amino-3-[4-(2-chlorobenzyl)-indol-3-yl]-4-methoxybutyric acid ethyl ester is obtained, that is used without further purification in the next stage.

c) 1,2,3,4-Tetrahydro-5-(2-chlorobenzyl)-4-methoxymethyl-β-carboline-3-carboxylic acid ethyl ester, 5.2 g (0.013 mol) of 2-amino-3-[4-(2-chlorobenzyl)-indol- 3-yl]-4-methoxybutyric acid ethyl ester is refluxed for one hour with 0.44 g of paraformaldehyde in 500 ml of toluene under argon on a water separator. Then it is filtered off from a turbidity. The evaporation residue is chromatographed on silica gel with equal parts of acetone and dichloromethane and yields 1 g (19% of theory) of 1,2,3,4-tetrahydro-5-(2-chlorobenzyl)-4-methoxymethyl-β-carboline-3-carboxylic acid ethyl ester.

d) 5-(2-Chlorobenzyl)-4-methoxymethyl-β-carboline-3-carboxylic acid ethyl ester, 1 g (0.0024 mol) of 1,2,3,4-tetrahydro-5-(2-chlorobenzyl)-4-methoxymethyl-β-carboline-3-carboxylic acid ethyl ester is mixed in a mixture of 20 ml of toluene and 7 ml of dichloromethane at −15° C. with 1.2 ml of triethylamine. Then 0.9 ml (0.0074 mol) of tert.butylhypochlorite, dissolved in 12 ml of dichloromethane, is instilled. The reaction mixture is stirred at room temperature for two more hours. The evaporation residue is chromatographed on silica gel with equal parts of acetone and dichloromethane and yields 0.33 g (33% of theory) of 5-(2-chlorobenzyl)-4-methoxymethyl-β-carboline- 3-carboxylic acid ethyl ester, melting point 182°–184° C. (from ethanol).

Analogously there are produced:

5-(4-Chlorobenzyl)-4-methoxymethyl-β-carboline-3-carboxylic acid ethyl ester, melting point 148°–150° C.;

5-(2-chlorobenzyl)-4-methyl-β-carboline-3-carboxylic acid ethyl ester from 4-(2-chlorobenzyl)-indole and 3-hydroxy- 2-nitrobutyric acid ethyl ester, melting point 192°–194° C.;

5-(4-chlorobenzyl)-4-ethyl-β-carboline-3-carboxylic acid ethyl ester from 5-(4-chlorobenzyl)-indole and 3-hydroxy- 2-nitrovaleric acid ethyl ester, melting point 265° C. (ethyl acetate);

5-(2-chlorobenzyl)-4-ethyl-β-carboline-3-carboxylic acid ethyl ester.

EXAMPLE 9

5-(2-Chlorobenzyl)-4-methoxymethyl-β-carboline-3-carboxylic acid isopropyl ester 0.2 g (5 mmol) of 5-(2-chlorobenzyl)-4-methoxymethyl-β-carboline-3-carboxylic acid ethyl ester is refluxed for 2 hours in 35 ml of isopropanol with 0.15 ml (0.5 mmol) of titanium tetraisopropylate. The mixture is filtered and the filtrate concentrated by evaporation to approximately a third. 0.112 g (54% of theory) of 5-( 2-chlorobenzyl)-4-methoxymethyl-β-carboline-3-carboxylic acid isopropyl ester crystallizes out, melting point 187°– 189° C.

Analogously there are produced:

5-(2-Chlorobenzyl)-4-methyl-β-carboline-3-carboxylic isopropyl ester, melting point 225°–228° C.; acid 5-(4-chlorobenzyl)-4-methoxymethyl-β-carboline-3-carboxylic acid isopropyl ester, melting point 177°–179° C.;

5-(2-chlorobenzyl)-4-ethyl-β-carboline-3-carboxylic acid isopropyl ester, melting point 218°–220° C. (ethyl acetate).

EXAMPLE 10

3-Benzoyl-5-(2-chlorobenzyl)-4-methoxymethyl-β-carboline a) 5-(2-Chlorobenzyl)-4-methoxymethyl-9-tosyl-β-carboline-3-carboxylic acid ethyl ester 0.744 g (0.0039 mol) of p-toluenesulfochloride is added under ice cooling to a solution of 1.2 g (0.0029 mol) of 5-(4-chlorobenzyl)-4-methoxymethyl-β-carboline-3-carboxylic acid ethyl ester, 0.16 g (0.0013 mol) of dimethylaminopyridine and 0.54 ml (0.0039 mol) of triethylamine in 120 ml of dichloromethane. The reaction mixture is stirred for another 15 minutes under ice cooling and then for 2 hours at room temperature. Then it is diluted with dichloromethane, washed with water, dried and concentrated by evaporation. The evaporation residue is crystallized under trituration with ether. The yield is 1.36 g (82% of theory) of 5-(2-chlorobenzyl)- 4-methoxymethyl-9-tosyl-β-carboline-3-carboxylic acid ethyl ester, melting point 140°–142° C.

b) 3-Benzoyl-5-(2-chlorobenzyl)-4-methoxymethyl-β-carboline

To a solution of 1.2 g (0.0021 mol) of 5-(2-chlorobenzyl)-4-methoxymethyl-9-tosyl-β-carboline-3-carboxylic acid ethyl ester in 60 ml of absolute tetrahydrofuran is slowly added 2.4 ml of a 2-molar solution of phenyllithium in bezene/ether at −70° C. under argon protection. The reaction mixture is stirred for another 15 minutes at −70° C. then for 3 hours at room temperature and finally for one hour at 35° C. The it is concentrated by evaporation. The residue is taken up in 150 ml of ethyl acetate. The solution in succession is washed with citric acid solution, water, sodium bicarbonate solution, water, saturated common salt solution and once more with water, dried and concentrated by evaporation. After chromatography on silica gel with equal parts of toluene and ethyl acetate and recrystallization from ethanol, 0.15 g (16% of theory) of 3-benzoyl-5-(2-chlorobenzyl)-4-methoxymethyl-β-carboline is obtained, melting point 147°–148° C.

Analogously there is produced:

3-Benzoyl-5-(4-chlorobenzyl)-4-methoxymethyl-β-carboline, melting point 174°–176° C.

EXAMPLE 11

6-Chloro-5-(4-chlorobenzyl)-4-methoxymethyl-3-(5-methoxymethylisoxazol- 3-yl)-β-carboline a) 5-(4-Chlorobenzyl)-4-methoxymethyl-β-carboline-3-methanol 0.5 g (0.00122 mol) of 5-(4-chlorobenzyl)-4-methoxymethyl-β -carboline-3-carboxylic acid ethyl ester is dissolved in 13 ml of toluene. To the solution cooled to −75° C. 2.3 ml of a 1,2-molar solution of diisobutylaluminiumhydride in toluene is slowly instilled under argon. It is stirred for 10 minutes more at −75° C., then for one hour at room temperature. 0.9 ml of methanol is slowly instilled to the reaction mixture again cooled to −75° C., it is stirred 10 minutes more, then 1.5 ml of a saturated potassium sodium tartrate solution is instilled. It is stirred for 20 minutes more at room temperature, then the mixture is extracted with ethyl acetate. The combined extracts are dried and concentrated by evaporation, the residue is recrystallized from ethanol. Thus 0.09 g (20% of theory) of 5-(4-chlorobenzyl)-4-methoxymethyl-β-carboline-3-methanol is obtained, melting point 220°–222° C.

b) 5-(4-chlorobenzyl)-4-methoxymethyl-β-carboline-3-carbaldehyde 1.3 g (0.00354 mol) of 5-(4-chlorobenzyl)-4-methoxymethyl-β -carboline-3-methanol is stirred for 192 hours under argon at room temperature with 1.74 g (0.02 mol) of manganese dioxide in 200 ml of dichloromethane. The manganese dioxide is suctioned off, the filtrate concentrated by evaporation and the residue recrystallized from ethanol. Thus 0.96 g (74% of theory) of 5-(4-chlorobenzyl)-4-methoxymethyl-β-carboline-3-carbaldehyde is obtained, melting point 248°–250° C.

c) 5-(4-Chlorobenzyl)-4-methoxymethyl-β-carboline-3-carbaldehyde-oxime 0.75 g (0.002 mol) of 5-(4-chlorobenzyl)-4-methoxymethyl-β -carboline-3-carbaldehyde is heated one hour to 105° C. with 0.18 g (0.0026 mol) of hydroxylaminehydrochloride in 19 ml of pyridine. 0.48 g (61% of theory) of 5-(4-chlorobenzyl)-4-methoxymethyl-β-carboline- 3-carbaldehyde-oxime is obtained from the evaporation residue after recrystallization from ethanol, melting point 224°–228° C.

d) 6-Chloro-5-(4-chlorobenzyl)-4-methoxymethyl-3-(5-methoxymethylisoxazol- 3-yl)-β-carboline 0.5 g (0.0013 mol) 5-(4-chlorobenzyl)-4-methoxymethyl-β -carboline-3-carbaldehyde-oxime is suspended in 25 ml of tetrahydrofuran and mixed with 5 ml of sodium hypochlorite solution under protective gas (argon). After 20 minutes no more initial material can be detected by thin-layer chromatography. 0.7 ml of methylpropargylether is instilled over 2.5 hours then the mixture is stirred for another hour. After it is left standing overnight it is diluted with ethyl acetate, washed neutral with water, dried and concentrated by evaporation. From the evaporation residue 0.031 g (5% of theory) of 6-chloro-5-(4-chlorobenzyl)-4-methoxymethyl-3-( 5-methoxymethylisoxazol-3-yl)-β-carboline, melting point 198°–200° C., is obtained by chromatography on silica gel and recrystallization from ethanol/ether.

EXAMPLE 12

6-Chloro-5-(4-chlorobenzyl)-4-methoxymethyl-3-(5-methoxymethylisoxazol- 3-yl)-β-carboline and 5-(2-chlorobenzyl)- 4-methoxymethyl-3-(5-methoxymethylisoxazol- 3-yl)-β-carboline a) 5-(2-Chlorobenzyl)-4- methoxymethyl-β-carboline-3-carbaldehyde-oxime The preparation takes place from 5-(2-chlorobenzyl)-4-methoxymethyl-β-carboline-3-carboxylic acid ethyl ester over alcohol and aldehyde, such as described for 5-( 4-chlorobenzyl)-4- methoxymethyl-β-carboline-3- carbaldehyde-oxime, melting point 209°–212° C.

b) 6-Chloro-5-(2-chlorobenzyl)-4-methoxymethyl-3-(5-methoxymethylisoxazol- 3-yl)-β-carboline and 5-(2-chlorobenzyl)- 4-methoxymethyl-3-(5-methoxymethylisoxazol- 3-yl)-β-carboline 1.06 g (0.0028 mol) of 5-(2-chlorobenzyl)-4-methoxymethyl-β -carboline-3-carbaldehyde-oxime in 25 ml tetrahydrofuran is mixed with 10 ml of sodium hypochlorite solution at 35° C. under argon. After 20 minutes no more initial material can be detected by thin-layer chromatography. 0.32 ml (0.004 mol) of methylpropargylether is instilled at room temperature and it is stirred for 3 more hours. After being left standing overnight it is diluted with ethyl acetate, washed neutral with water, dried and concentrated by evaporation. The residue is chromatographically separated on silica gel with a mixture of 2 parts tetrahydrofuran and one part of toluene. First a fraction is isolated, which after recrystallization from a dichloromethane/cyclohexane mixture yields 0.1 g (8% of theory) of 5-(2-chlorobenzyl)-4-methoxymethyl-3-(5-methoxymethylisoxazol- 3-yl)-β-carboline, melting point 178°–180° C.

From a more slowly running fraction 0.06 g (5% of theory) of 6-chloro-5-(2-chlorobenzyl)-4-methoxymethyl-3-( 5-methoxymethylisoxazol-3-yl)-β-carboline, melting point 238°–240° C. (from ethanol) is obtained.

EXAMPLE 13

5-(2-Chlorobenzyl)-4-methoxyethoxymethyl-β-carboline-3-carboxylic acid-isopropyl ester a) 2-Nitro-3-hydroxy-5,8-dioxa-pelargonic acid ethyl ester.

To a solution of 4 g (0.034 mol) methoxyethoxyacetaldehyde in 20 ml of ethanol 4.5 g (0.034 mol) nitroacetic acid ethyl acetate is instilled under ice cooling. The mixture is stirred for one hour under cooling, then left overnight at room temperature. The solution is concentrated by evaporation and the residue is taken up in ether. This solution is first washed with water, then with sodium hydrogenphosphate solution and finally with water one more time, dried and concentrated by evaporation. 4.5 g (53 of theory) of 2-nitro- 3-hydroxy-5,8-dioxa-pelargonic acid ethyl ester remains in the form of a light yellow liquid.

b) 3-[4-(2-chlorobenzyl)-indol-3-yl]-2-nitro-5,8-dioxapelargonic acid ethyl ester 0.5 g (0.0021 mol) of 4-(2-chlorobenzyl)-indole is refluxed for 4 hours under argon in a mixture of 20 ml of toluene and 1.3 ml of acetic acid with 2 g (0.008 mol) of 2-nitro-3-hydroxy-5-8-dioxa-pelargonic acid ethyl ester.

The reaction mixture is concentrated by evaporation, the residue is dissolved in ethyl acetate, washed with sodium carbonate solution, the solution is dried and concentrated by evaporation. 0.59 g (69% of theory) of 3-[4-(2-chlorobenzyl)-indol-3-yl]-2-nitro-5,8-dioxa-pelargonic acid ethyl ester is obtained from the residue by chromatography on silica gel with cyclohexane/ethyl acetate.

c) 2-Amino-3-[4-(2-chlorobenzyl)-indol-3-yl]-5,8-dioxapelargon acid ethyl ester

According to the process described under 8b 13.3 g (85% of theory) of 2-amino-3-[4-(2-chlorobenzyl)-indol-3-yl]-5,8-dioxa-pelargonic acid ethyl ester is obtained from 17 g of 3-[4-(2-chlorobenzyl)-indol-3-yl]-2-nitro- 5,8-dioxa-pelargonic acid ethyl ester.

d) 1,2,3,4-Tetrahydro-5-(2-chlorobenzyl)-4-methoxyethoxymethyl-β -carboline-3-carboxylic acid ethyl ester According to the process described under 8c 1,2,3,4-tetrahydro- 5-(2-chlorobenzyl)-4-methoxyethoxymethyl-β-carboline- 3-carboxylic acid ethyl ester is obtained from 2-amino-3-[4-(2-chlorobenzyl)-indol-3-yl]-5,8-dioxa-pelargonic acid ethyl ester.

e) 5-(2-Chlorobenzyl)-4-methoxyethoxymethyl-β-carboline- 3-carboxylic acid ethyl ester According to the process described under 8d the compound is produced from 1,2,3,4-tetrahydro-5-(2-chlorobenzyl)- 4-methoxymethyl-β-carboline-3-carboxylic acid ethyl ester.

f) 5-(2-Chlorobenzyl)-4-methoxyethoxymethyl-β-carboline- 3-carboxylic acid isopropyl ester The transesterification of 5-(2-chlorobenzyl)-4-methoxyethoxymethyl-β -carboline-3-carboxylic acid ethyl ester to isopropyl ester takes place according to the process described in example 9. The yield of 5-(2-chlorobenzyl)-4-methoxyethoxymethyl-β-carboline-3-carboxylic acid isopropyl ester is 62%, melting point 145°–146° C. (ethyl acetate).

EXAMPLE 14

5-(2-Chlorobenyl)-3-cyclopropylcarbonyl-4-methoxyethoxymethyl-β -carboline a) 5-(2-Chlorobenzyl)-4-methoxyethoxymethyl-β-carboline- 3-carboxylic acid The acid is obtained by saponification from 5-(2-chlorobenzyl)- 4-methoxyethoxymethyl-β-carboline-3-carboxylic acid ethyl ester with 2n sodium hydroxide solution in boiling ethanol.

b) 5-(2-Chlorobenzyl)-4-methoxyethoxymethyl-β-carboline- 3-carboxylic acid imidazolide 1.5 g (0.0022 mol) of imidazole in 20 ml of tetrahydrofuran is mixed with 0.4 ml (0.0054 mol) of thionylchloride dissolved in 5 ml of tetrahydrofuran. The precipitate is suctioned off, the filtrate is instilled in a suspension of 0.693 g (0.00163 mol) of 5-( 2-chlorobenzyl)-4-methoxyethoxymethyl-β-carboline-3-carboxylic acid in 30 ml of tetrahydrofuran. After it is left standing overnight the solvent is distilled off, the residue is dissolved in ethyl acetate, the solution is washed imidazole free with water. After concentration by evaporation 0.55 g (71% of theory) of 5-(2-chlorobenzyl)- 4-methoxyethoxymethyl-β-carboline-3-carboxylic acid imidazolide remains.

c) 5-(2-Chlorobenzyl)-3-cyclopropylcarbonyl-4-methoxyethoxymethyl-β -carboline

A solution of 0.5 g of 5-(2-chlorobenzyl)-4-methoxyethoxymethyl-β -carboline-3-carboxylic acid imidazolide is instilled under argon at −10° C. in a solution of cyclopropylmagnsesium bromide produced from 0.153 g of magnesium and 0.764 g of cyclopropyl bromide in 5 ml of tetrahydrofuran. A clear solution results, that decomposes with ice water and is worked up in the usual way. The crude product is chromatographed on silica gel with a 1:1 mixture of toluene and ethyl acetate. After recrystallization from ethyl acetate, 0.15 g (32% of theory) of 5-(2-chlorobenzyl)-3-cyclopropylcarbonyl- 4-methoxyethoxymethyl-β-carboline, melting point 158°–160° C., is obtained.

The preceding examples can be repeated with similar success by substituting the generically or specifically described reactants and/or operating conditions of this invention for those used in the preceding examples.

From the foregoing description, on skilled in the art can easily ascertain the essential characteristics of this invention, and without departing from the spirit and scope thereof, can make various changes and modifications of the invention to adapt it to various usages and conditions.

We claim:

1. A compound of formula I

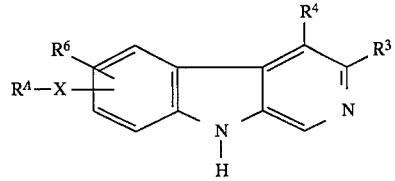

wherein $R^A$ is a pyridine, furan, thiophene, pyrrole, thiazole, imadizole, benzofuran, benzimidazole, quinoline, isoquinoline, phenyl, biphenyl, naphthyl or indenyl ring, not attached through a heteroatom, and optionally independently substituted by one or two of halogen, $C_{1-4}$-alkoxy, $C_{1-4}$-alkyl or amino, X is $-(CH_2)_n-$ or $-C\equiv C-$ $R^6$ is hydrogen, halogen or $C_{1-4}$-alkoxy, $R^4$ is hydrogen, $C_{1-4}$-alkyl or $-(CH_2)_m-O-(CH_2)_p-R$, $R^3$ is $-CO_2-C_{1-6}$-alkyl$-CO-R^2$, $-COOH$ or

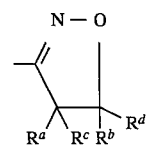

n is 0, 1 or 2, m is 1 or 2,

P is 1, 2, 3 or 4,

R is hydrogen or $C_{1-2}$-alkoxy $R^2$ is $C_{1-4}$-alkyl or $C_{3-7}$-cycloalkyl each optionally substituted by methyl, or is a mono- or bicyclic $C_{6-12}$-aryl radical optionally substituted by $C_{1-4}$-alkyl, $C_{1-4}$alkoxy or amino, $R^a$ and $R^b$ are each independently hydrogen, $C_{1-6}$-alkoxy, $C_{1-6}$-alkyl, $-CH_2-O-C_{1-4}$-alkyl, phenyl or benzyl and $R^c$ and $R^d$ each mean a hydrogen or together a bond, or an isomer or acid addition salt thereof with the provisos that (a) $R^A$ is not 6-(1-pyrrolyl), and (b) $R^3$ is not $-COOC_2H_5$:

(i) if $R^6$ is hydrogen, $R^4$ is hydrogen and $-X-R^A$ is 6-phenethinyl, 5-phenyl or 5-benzyl;

(ii) if $R^6$ is hydrogen, $R^4$ is methyl and $-X-R^A$ is benzyl, phenyl, or 6-phenylethyl; or (iii) if $R^6$ is hydrogen, $R^4$ means methoxymethyl and $-X-R^A$ means 5-benzyl.

2. A compound according to claim 1, wherein $R^A$ is a pyridine, furan, thiophene, pyrrole, thiazole, imadizole, benzofuran, benzimidazole, quinoline, isoquinoline, phenyl, biphenyl, naphthyl or indenyl ring, attached through a ring carbon atom, and optionally independently substituted by one or two of halogen, $C_{1-4}$-alkoxy, $C_{1-4}$-alkyl or amino.

3. A pharmaceutical composition comprising an effective amount of a compound according to claim 1 and a pharmaceutically acceptable carrier.

4. A method of treating anxiety, comprising administering an effective amount of a compound of claim 1.

5. 5-(2-Thienyl)-4-methoxymethyl-β-carboline-3-carboxylic acid isopropyl ester;

5-(3-pyridyl)-4-methoxymethyl-β-carboline-3-carboxylic acid isopropyl ester;

6-(4-chlorophenylethynyl)-4-methoxymethyl-β-carboline- 3-carboxylic acid isopropyl ester;

6-(4-chlorophenyl-ethyl)-4-methoxymethyl-β-carboline-3-carboxylic acid isopropyl ester;

5-(4-chlorobenzyl)-4-methoxymethyl-β-carboline-3-carboxylic acid isopropyl ester;

3-benzoyl-5-(2-chlorobenzyl)-4-methoxymethyl-β -carboline;

5-(2-chlorobenzyl)-4-methoxymethyl-3-(5-methoxymethylisoxazol- 3-yl)-β-carboline- 6-(2-pyridylethyl)-4-methoxymethyl-β-carboline-3-carboxylic acid isopropyl ester; or 5-(2-chlorobenzyl)-3-cyclopropylcarbonyl-4-methoxymethyl-β -carboline.

\* \* \* \* \*